(12) United States Patent
Birkhoelzer et al.

(10) Patent No.: US 7,926,088 B2
(45) Date of Patent: Apr. 12, 2011

(54) METHOD FOR MANAGING DATA RECORDS WITH PERSON-RELATED CONTENTS BY MEANS OF A COMPUTER SYSTEM

(75) Inventors: Thomas Birkhoelzer, Radolfzell (DE); Frank Krickhahn, Herzogenaurach (DE); Juergen Vaupel, Weisendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1253 days.

(21) Appl. No.: 10/348,019

(22) Filed: Jan. 22, 2003

(65) Prior Publication Data

US 2003/0196124 A1 Oct. 16, 2003

(30) Foreign Application Priority Data

Jan. 22, 2002 (DE) .................................. 102 02 286

(51) Int. Cl.
*G06F 7/04* (2006.01)
*G06F 7/06* (2006.01)
(52) U.S. Cl. .............................. 726/4; 713/179; 713/165
(58) Field of Classification Search .................... None
See application file for complete search history.

(56) References Cited

U.S. PATENT DOCUMENTS

| | | | |
|---|---|---|---|
| 5,867,821 A * | 2/1999 | Ballantyne et al. | 705/2 |
| 6,208,374 B1 * | 3/2001 | Clinch | 348/79 |
| 6,347,329 B1 * | 2/2002 | Evans | 709/202 |
| 6,606,413 B1 * | 8/2003 | Zeineh | 382/232 |
| 6,609,206 B1 * | 8/2003 | Veneklase | 726/7 |
| 6,874,085 B1 * | 3/2005 | Koo et al. | 713/165 |
| 6,941,271 B1 * | 9/2005 | Soong | 705/3 |
| 6,959,289 B1 * | 10/2005 | James et al. | 705/51 |
| 7,080,409 B2 * | 7/2006 | Eigeles | 726/28 |
| 7,185,206 B2 * | 2/2007 | Goldstein | 713/189 |

FOREIGN PATENT DOCUMENTS

| | | |
|---|---|---|
| DE | 10008153 | 6/2001 |
| JP | 61-226848 A | 10/1986 |
| JP | 06223122 A | 8/1994 |
| JP | 9-81519 A | 3/1997 |
| JP | 2000-148886 A | 5/2000 |
| JP | 2001-167201 A | 6/2001 |
| JP | 2001-243403 A | 9/2001 |
| JP | 2001-325249 A | 11/2001 |
| JP | 2001-338058 A | 12/2001 |
| WO | WO 96/08755 A1 | 3/1996 |

OTHER PUBLICATIONS

Oleg S. Pianykh, "Where Do You Get DICOM from?", Digital Imaging and Communications in Medicine (DICOM), 2008, Springer Berlin Heidelberg, pp. 11-16.*

*Primary Examiner* — Michael Pyzocha
*Assistant Examiner* — Jeffery Williams
(74) *Attorney, Agent, or Firm* — Harness, Dickey & Pierce, P.L.C.

(57) ABSTRACT

A computer system receives from a user computer, an authorization code and an access instruction for at least one data record with person-related contents. It executes the access instruction only if the authorization code matches a comparison criterion which it determines on the basis of a data record code assigned to the data record. The data record code is specific at least to the person whose personal data the data record contains.

15 Claims, 4 Drawing Sheets

U.S. PATENT DOCUMENTS

| | | | |
|---|---|---|---|
| 7,213,266 B1 * | 5/2007 | Maher et al. | 726/26 |
| 7,234,160 B2 * | 6/2007 | Vogel et al. | 726/10 |
| 7,376,836 B2 * | 5/2008 | Graves et al. | 713/168 |
| 2001/0032100 A1 * | 10/2001 | Mahmud et al. | 705/2 |
| 2001/0041991 A1 * | 11/2001 | Segal et al. | 705/3 |
| 2002/0010679 A1 * | 1/2002 | Felsher | 705/51 |
| 2002/0019751 A1 * | 2/2002 | Rothschild et al. | 705/3 |
| 2002/0029157 A1 * | 3/2002 | Marchosky | 705/3 |
| 2002/0052551 A1 * | 5/2002 | Sinclair et al. | 600/476 |
| 2002/0109735 A1 * | 8/2002 | Chang et al. | 345/853 |
| 2002/0133495 A1 * | 9/2002 | Rienhoff et al. | 707/100 |
| 2002/0138471 A1 * | 9/2002 | Dutta et al. | 707/3 |
| 2002/0161795 A1 * | 10/2002 | O'Rourke | 707/500 |
| 2003/0074564 A1 * | 4/2003 | Peterson | 713/182 |
| 2003/0115142 A1 * | 6/2003 | Brickell et al. | 705/51 |
| 2003/0131235 A1 * | 7/2003 | Wheeler et al. | 713/168 |
| 2003/0154411 A1 * | 8/2003 | Hovik | 713/202 |
| 2003/0158754 A1 * | 8/2003 | Elkind | 705/3 |

* cited by examiner

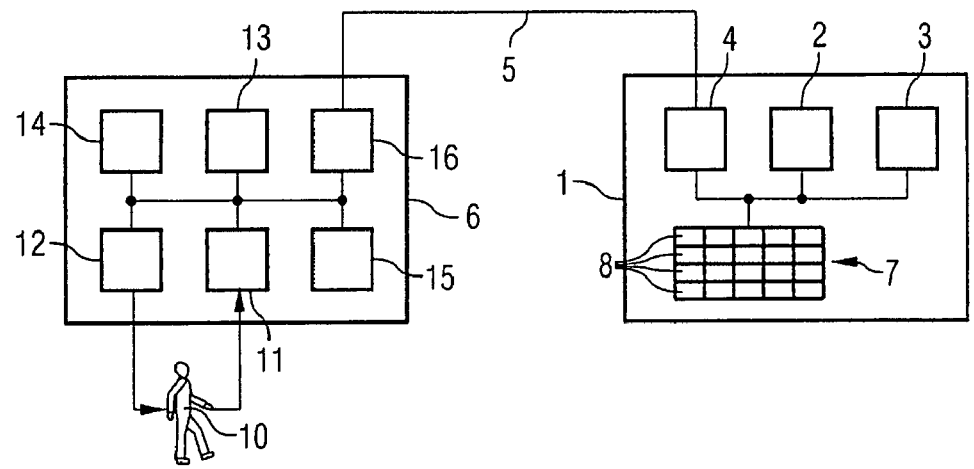

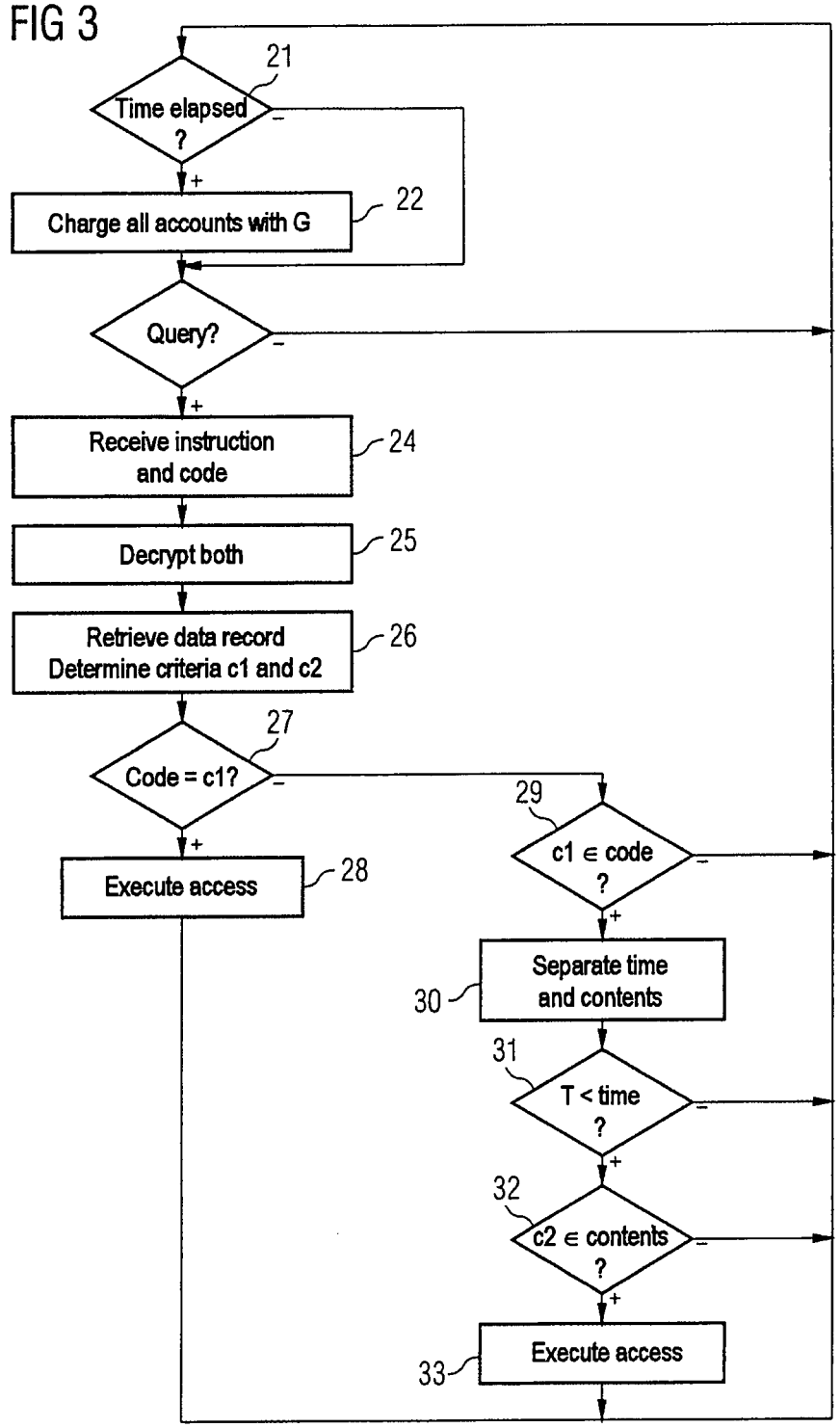

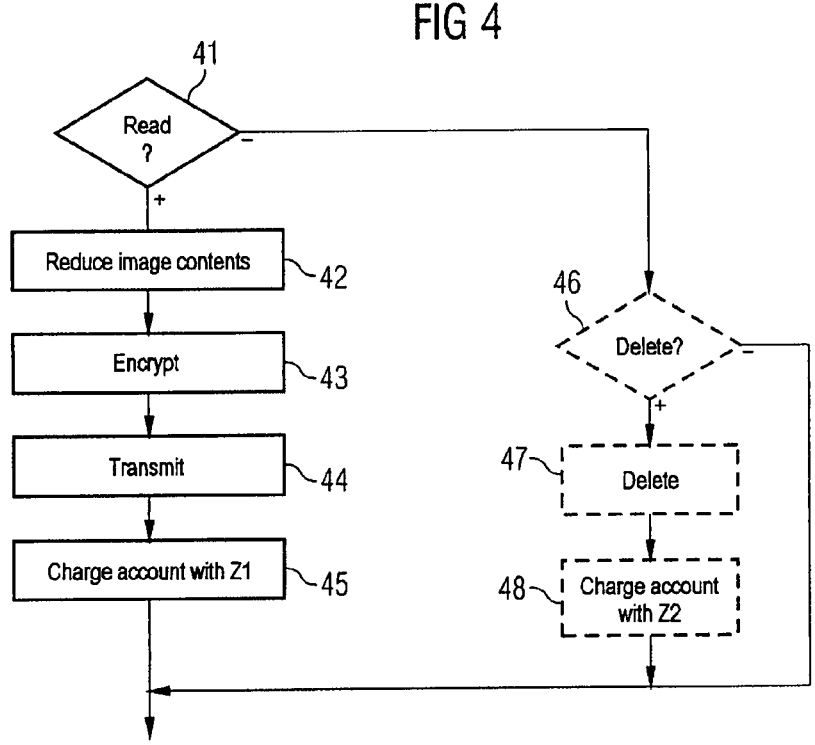

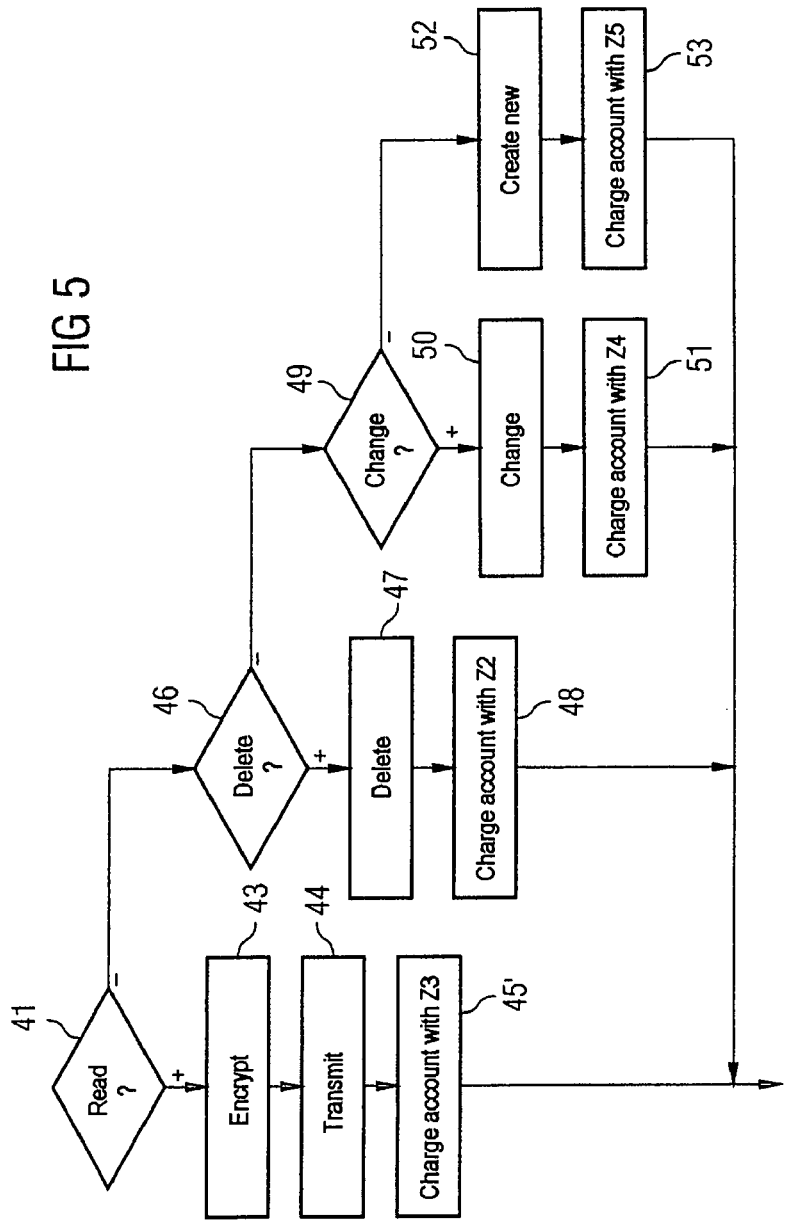

METHOD FOR MANAGING DATA RECORDS WITH PERSON-RELATED CONTENTS BY MEANS OF A COMPUTER SYSTEM

The present application hereby claims priority under 35 U.S.C. §119 on German patent application number DE 10202286.0 filed Jan. 22, 2002, the entire contents of which are hereby incorporated herein by reference.

FIELD OF THE INVENTION

The present invention generally relates to a method for managing data records with person-related contents by use of a computer system. Preferably, the computer system receives from a user computer, an authorization code and an access instruction for at least one data record, and preferably the computer system executes the access instruction only if the authorization code matches a comparison criterion.

BACKGROUND OF THE INVENTION

Management methods are generally known. In particular, official registers that can be queried remotely (e.g. criminal record registers such as the German central federal register or the German register of traffic offenders) are managed in this way.

A method for managing data records by using a computer system is known from DE 100 08 153 A1. The data records can have person-related contents here. The computer system receives an authorization code and an access instruction for at least one data record. It then executes the access instruction only if the authorization code matches a comparison criterion which is determined by the computer system on the basis of a data record code assigned to the data record. The data record code is specific to the persons permitted to access the data record.

Similar databases with a plurality of (e.g. X-ray) images are used in the medical field too. These databases are operated and managed by the respective health service provider (e.g. a hospital).

The access to data records held in such databases is sufficient if the query is performed within the health service provider. However, if the person whose data are contained in the data records changes health service provider (e.g. as a result of a move, a different treatment reason or dissatisfaction with the previous service provider), the problem of enabling a new health service provider access to the already existing data records arises. Moreover, the problem that the respective person often does not know themself whether and what data records about them are stored additionally arises in this connection.

It has already been proposed to set up central databases (possibly as part of an electronic patient file) in which the data generated in each case by all health service providers can be stored. Such approaches, however, present two problems.

On the one hand a complete and comprehensive solution is very complex. On the other hand a partial solution which covers only some of the health service providers presents the same basic problem already outlined above in connection with one service provider. The same problem of access would arise in the event of a person changing to a service provider that is not part of this database system.

In addition, the question of who should operate these databases arises. In this regard, it has previously been proposed that either the health service providers or the health insurance companies should do so. However, patients can change both health service provider and health insurance company. The problem of orderly access thus arises again in this case too.

SUMMARY OF THE INVENTION

An object of an embodiment of the present invention is therefore to provide a congeneric method for managing data records—in particular with medical contents—by which a generally accessible database archive can be managed while maintaining the necessary confidentiality of the personal data stored in the data records.

An object may be achieved in that the comparison criterion is determined by the computer system on the basis of a data record code assigned to the data record and that the data record code is specific at least to the person whose personal data the data record contains.

In this way access is then only possible with the—implicit or explicit—agreement of the person whose personal data are stored in the data records.

The comparison criterion can be exclusively person-specific or can comprise an exclusively person-specific sub-criterion and a further sub-criterion.

The first case, an exclusively person-specific comparison criterion, is provided in particular for the self-management of the data records by the respective person. For this reason, in this case transmissions to the user computer are possible, but not changes in the data records. Deletions of data records may be permitted in some circumstances. Furthermore, it is not necessary to transmit complete data records to the user computer for the communication between the user computer and the computer system. Rather, a limited transmission of the data record is sufficient. If the data record contains an image, the image can be transmitted to the user computer with only reduced image contents for example.

The division of the comparison criterion into a person-specific and a further sub-criterion is intended in particular for the access by a health service provider. In particular, the second sub-criterion can be time-specific and/or content-specific with respect to the data record. For example, a code which is firstly person-specific and secondly time-specific can be transmitted to a health service provider by the patient whose data are stored in the data records. The transmission may be performed, for example, by handing over a chipcard, by stating a password, or in another way. The health service provider adds to this code a code assigned to the provider personally, on the basis of which the provider's authorizations are defined for example. In this way ophthalmologists may be allocated different access codes than dentists for example.

In particular for the patient, a combination of this type increases the access security to prevent misuse of the patient's data. In this way, for example, it is then possible to enable an ophthalmologist to access data records with ophthalmological and possibly supplementary general medical findings for one day. Access to other findings, e.g. of a dental or orthopedic nature, can on the other hand also be excluded in this case.

The health service provider requires of course full access to the data records. In particular, he is able to retrieve data records without restriction, not just to delete and retrieve them to a limited extent. In this case images are transmitted to the user computer with complete image contents, for example. It is also possible to change existing data records or create new data records.

For data security reasons, the computer system encrypts the data record before transmission to the user computer.

If the computer system decrypts at least the authorization code following reception, that is to say the latter is transmitted in encrypted form, an unauthorized access to the data records can be prevented even more reliably.

If the computer system communicates with the user computer via a point-to-point connection, any interception of the transmitted authorization code is furthermore impossible, or possible only with great difficulty.

The management of the data records is of course costly in terms of time and money. An account assigned to the data record is therefore preferably charged with a basic debit amount at periodic intervals. It is furthermore possible to charge the account with an access debit amount as a result of the execution of the access instruction. This can be cost-dependent in this case.

BRIEF DESCRIPTION OF THE DRAWINGS

Further advantages and details emerge from the description of an exemplary embodiment below with reference to the drawings, in which, in a basic representation:

FIG. 1 shows a computer network;
FIG. 2 shows a data record;
FIG. 3 shows a flowchart; and
FIGS. 4 and 5 show details of FIG. 3.

DETAILED DESCRIPTION OF THE PREFERRED EMBODIMENTS

According to FIG. 1, a computer system 1 has a main unit 2. The main unit 2 processes a computer program product 3. The computer system 1 is therefore programmed with the computer program product 3.

Under the control of the computer program product 3, the computer system 1 communicates via an interface 4 and a point-to-point connection 5 with a user computer 6. It furthermore accesses a database generally denoted by 7. Data records 8 are stored in the database 7. The contents of the data records 8 are medical. Their structure is described in greater detail below with reference to FIG. 2.

According to FIG. 2, every data record 8 contains one or more images 9. Three X-ray images 9 of a hand, or of 2 fingers respectively, are schematically represented in FIG. 2. The data record 8 furthermore contains a number of bibliographical particulars. Said particulars comprise a creation date (e.g. Jan. 1, 2001), the name of a patient of whom the recordings were taken (e.g. Peter Müller), and the name of the attending physician (e.g. Dr. Meyer). The data record 8 furthermore comprises particulars of the location of the recording (e.g. Munich), the diagnosis (e.g. knuckle fracture) made by the attending physician, and the specification of which part of the body, in this case the hand, the X-ray recordings were taken. Finally, the data record 8 contains a further two data record codes $c_1$, $c_2$. Access authorizations to the data record 8 are checked by means of the data record codes $c_1$, $c_2$. The data record 8 also furthermore contains the number of an assigned account (4711-007).

The first data record code $c_1$ is person-specific. It therefore contains in encrypted form the specification that the data contained in the data record 8 are of a medical nature about Peter Müller. The second data record code $c_2$ is content-specific for the data record 8. It specifies, for example, that it relates to a bone fracture which could be significant on the one hand in the general medical field and on the other hand in the orthopedic field.

A user 10 can communicate interactively with the user computer 6 via a conventional input device 11 and a conventional output device 12. The user computer 6 also has a main unit 13 which processes a control program in the form of a conventional computer program product 14. The user computer 6 furthermore has a storage device 15 for buffering data as well as an interface 16 which represents the second end point of the point-to-point connection 5. The computer system 1 and the user computer 6 thus communicate with one another via the two interfaces 4, 16 and the point-to-point connection 5. The communication between computer system 1 and the user computer 6 will be described—from the point of view of the computer system 1—below with reference to FIG. 3.

As will be immediately apparent, the flowchart represented in FIG. 3 is executed cyclically. During the course of processing the flowchart, first of all a query is issued in a step 21 as to whether a basic time has elapsed. If so, all accounts are charged with a basic debit amount G in a step 22. This charging is thus performed at periodic intervals.

Otherwise a branch is made directly to a step 23 in which it is checked whether an access instruction and an authorization code were transmitted from the user computer 6. If not, a branch is made to step 21 again, otherwise steps 24 to 27 are executed.

In step 24 the computer system 1 receives from the user computer 6—via a web interface for example—the access instruction for the desired data record 8 and an authorization code. In step 25 it then decrypts said two particulars. In step 26 it then retrieves the desired data record 8 from the database 7 and determines the data record code $c_1$, $c_2$ on the basis of said data record 8. It is then checked in step 27 whether the transmitted authorization code is identical to the data record code $c_1$. If so, the desired access is executed in a step 28. In this case, therefore, the comparison criterion is exclusively person-specific. It is determined on the basis of the data record code $c_1$ assigned to the data record 8.

Otherwise a branch is made to a step 29. In step 29 it is checked whether the transmitted authorization code contains the data record code $c_1$. The check in step 29 thus corresponds to a check of a person-specific first sub-criterion. If the transmitted authorization code does not pass the check in step 29, a branch is made directly to step 21 again, otherwise execution continues with steps 30 and 31.

In step 31 a time limit and a contents code are separated out of the transmitted authorization code. The contents code can be formed here by, for example, a service provider code assigned to a particular health service provider. In step 31 it is checked whether a time T determined internally by the computer system 1 is still less than the time limit determined in step 30. If not, a branch is made directly to step 21 again, otherwise to step 32.

In step 32 it is checked whether the contents code determined in step 30 contains the code $c_2$. If so, the desired access is executed in a step 33, otherwise a branch is made to step 21.

The check in steps 31 and 32 is thus the check for a further sub-criterion which is both time-specific and content-specific with respect to the requested data record 8. In both cases, that is to say both when executing the access in accordance with step 28 and when executing the access in accordance with step 33, the access instruction is however executed only if the transmitted authorization code matches the comparison criterion.

The access instructions in accordance with steps 28 and 33 are described in greater detail below with reference to FIGS. 4 and 5. In these figures, the access in accordance with step 28 is shown in greater detail in FIG. 4, and the access in accordance with step 33 is shown in FIG. 5.

According to FIG. 4, for the execution of step 28, first of all it is queried in a sub-step 41 whether the transmitted access instruction is a read instruction. If so, first of all the image contents of the images 9 are reduced in a sub-step 42. The contents of the data record 8 are then encrypted in a sub-step 43 before it is transmitted in a sub-step 44 to the user computer 6. In this case, therefore, the data record 8 is transmitted to the user computer 6 only to a limited extent. In particular, the images 9 are transmitted without diagnostic image quality. Finally, the account assigned to the data record 8 is charged with an additional debit amount Z1 in a sub-step 45.

If the check in sub-step 41 indicated that no transmission to the user computer 6 was desired, a branch is made to a sub-step 46. In sub-step 46 it is checked whether the access instruction is a delete instruction. If this check returns a positive response, the delete instruction is executed in a sub-step 47. The assigned account is then charged with an additional debit amount Z2 in a sub-step 48.

If the check in sub-step 46 also returns a negative response, the step 28 is exited without further actions.

It is possible to restrict the permitted accesses to the data record 8 to the reading and transmission to the user computer 6. In this case, the sub-steps 46 to 48 can be omitted. For this reason, they are indicated in FIG. 4 by dashed lines only. What is paramount is that the data record 8 cannot be changed by the access instruction in the course of step 28.

Where the same actions are executed in the course of step 33 as in the course of step 28, the individual elements in FIG. 5 are denoted by the same reference numerals. Only what is different from FIG. 4 will therefore be discussed below with reference to FIG. 5.

In the course of reading and transmitting the data record 8 to the user computer 6, firstly the sub-step 42 is omitted. The requested data record 8 is thus transmitted in its entirety, and consequently in particular also the images 9 with complete image contents, to the user computer 6. Since the execution of the sub-steps 43 and 44 in the course of step 33 may entail a different cost than the execution of the sub-steps 42 to 44 in the course of step 28, a sub-step 45' is executed instead of the sub-step 45. In the sub-step 45', although the assigned account is likewise charged with an additional debit amount Z3, said additional debit amount Z3 may differ from the additional debit amount Z1.

According to FIG. 5, a deletion of the data record 8 is also possible in the course of executing step 33. Furthermore, if the data record 8 is neither to be transmitted to the user computer 6 nor deleted, in sub-step 46 a branch is made to a sub-step 49. In sub-step 49 it is queried whether the desired data record 8 is to be changed. If so, the change is performed in a sub-step 50 and the account is again charged with an additional debit amount Z4 in a sub-step 51.

If the data record 8 is neither to be transmitted to the user computer 6, nor deleted, nor changed, it can only be newly created. This new creation is performed in a sub-step 52. In a sub-step 53 the account is again charged with an additional debit amount Z5.

The individual additional debit amounts Z1 to Z5 may differ from one another. In particular they can reflect the cost incurred by the execution of the prior sub-steps 42 to 44, or 43 and 44, 47, 50 and 52 respectively.

The communication between the computer system 1 and the user computer 6 can be carried out, for example, in accordance with https or in accordance with SSL. The format in which the transmissions are carried out can be the DICOM format for example.

The management method described above enables in a simple manner a universal, patient-centered storage of data records 8, while at the same time ensuring the necessary data security.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for managing data records with person-related contents using a computer system, comprising:

receiving, in the computer system from a user computer, an authorization code and an access instruction for at least one data record;

checking whether the authorization code is identical to a first data record code, said first data record code being specific to personal data contained in the data record;

checking whether the authorization code contains said first data record code and a second data record code when the authorization code is not identical to the first data record code, said second data record code being content-specific to the data record;

transmitting an image contained in said data record with a first image content to the user computer when the authorization code is identical to the first data record code and said access instruction is a read access instruction; and transmitting said image with a second image content to the user computer when the authorization code contains the first data record code and the second data record code and said access instruction is a read access instruction, wherein said first image content is reduced relative to said second image content.

2. The management method as claimed in claim 1, wherein in the case that the authorization code is identical to the first data record and the access instruction is not a read access instruction, the data record is not changed.

3. The management method as claimed in claim 1, wherein the computer system encrypts the data record before transmission to the user computer.

4. The management method as claimed in claim 1, wherein in the case that the authorization code contains the first data record code and the second data record code and the access instruction is not a read access instruction the data record is at least one of deleted, changed and newly created.

5. The management method as claimed in claim 1, wherein the computer system decrypts at least the authorization code following reception.

6. The management method as claimed in claim 1, wherein the computer system communicates with the user computer via a point-to-point connection.

7. The management method as claimed in claim 1, wherein the contents of the data record are medical.

8. The management method as claimed in claim 1, wherein an account assigned to the data record is charged with a basic debit amount at periodic intervals.

9. The management method as claimed in claim 8, wherein, as a result of the execution of the access instruction, the account is charged with an access debit amount.

10. The management method as claimed in claim 9, wherein the access debit amount is cost-dependent.

11. A non-transitory computer readable medium storing a program that when executed on a computer causes the computer to perform the method for managing data records as defined in claim 1.

12. A non-transitory computer readable medium storing a program that when executed on a computer causes the computer to perform the method for managing data records as defined in claim 2.

13. A non-transitory computer readable medium storing a program that when executed on a computer causes the computer to perform the method for managing data records as defined in claim 4.

14. A non-transitory computer readable medium storing a program that when executed on a computer causes the computer to perform the method for managing data records as defined in claim 9.

15. The management method as claimed in claim 1, wherein the first image content has a reduced resolution and the second data content has a full resolution.

* * * * *